United States Patent
Guy

(10) Patent No.: US 10,514,341 B2
(45) Date of Patent: Dec. 24, 2019

(54) SYSTEM AND METHOD OF DETECTING UNDERGROUND GAS LEAKAGE

(71) Applicant: Utilis Israel Ltd., Rosh HaAyin (IL)

(72) Inventor: Lauren Guy, Beer-Shava (IL)

(73) Assignee: Utilis Israel Ltd., Rosh HaAyin (IL)

( * ) Notice: Subject to any disclaimer, the term of this patent is extended or adjusted under 35 U.S.C. 154(b) by 371 days.

(21) Appl. No.: 15/440,054

(22) Filed: Feb. 23, 2017

(65) Prior Publication Data

US 2017/0176350 A1 Jun. 22, 2017

Related U.S. Application Data

(63) Continuation-in-part of application No. 15/014,053, filed on Feb. 3, 2016, now Pat. No. 9,945,942, which
(Continued)

(51) Int. Cl.
*G01M 3/18* (2006.01)
*G01N 22/00* (2006.01)
(Continued)

(52) U.S. Cl.
CPC ............ *G01N 22/00* (2013.01); *G01M 3/183* (2013.01); *G01N 33/18* (2013.01); *G01S 7/025* (2013.01);
(Continued)

(58) Field of Classification Search
CPC ....... G01M 3/183; G01N 22/00; G01N 33/18; G01S 7/025; G01S 13/867; G01V 3/12; G01V 11/00; G01V 9/02; Y02A 90/344
(Continued)

(56) References Cited

U.S. PATENT DOCUMENTS 2,884,624 A * 4/1959 En Dean ............... G01M 3/005
166/250.08
3,623,111 A 11/1971 Provencher et al.
(Continued)

FOREIGN PATENT DOCUMENTS

CN 102819047 12/2012
CN 103748318 4/2014
(Continued)

OTHER PUBLICATIONS

Office Action of U.S. Appl. No. 15/014,053 dated Oct. 27, 2017.
(Continued)

*Primary Examiner* — John E Breene
*Assistant Examiner* — Jeffrey P Aiello
(74) *Attorney, Agent, or Firm* — Pearl Cohen Zedek Latzer Baratz LLP

(57) ABSTRACT

A system and a method may detect underground water or gas leakage. The method may include receiving a first scan of an area including an underground gas pipe at a first polarization, the first scan including first microwave reflections of the area at a wavelength range of 3.8 cm to 1.3 m; receiving additional data, filtering electromagnetic noise from the first scan using the additional data; creating a water roughness map based on typical roughness values of a set of types of water sources and the filtered first scan; identifying one or more water accumulations at one or more locations along the gas pipe using the water roughness map and the filtered first scan and calculating the water content at the one or more locations along the gas pipe based on the identified one or more water accumulations.

15 Claims, 13 Drawing Sheets

Related U.S. Application Data is a continuation-in-part of application No. 14/666,648, filed on Mar. 24, 2015, now Pat. No. 9,285,475.

(51) Int. Cl.

| | |
|---|---|
| *G01N 33/18* | (2006.01) |
| *G01V 3/12* | (2006.01) |
| *G01S 7/41* | (2006.01) |
| *G01V 9/02* | (2006.01) |
| *G01V 11/00* | (2006.01) |
| *G01S 13/90* | (2006.01) |
| *G01S 7/02* | (2006.01) |
| *G01V 8/00* | (2006.01) |
| *G01S 13/86* | (2006.01) |

(52) U.S. Cl.
CPC ............... *G01S 7/411* (2013.01); *G01S 13/90* (2013.01); *G01V 3/12* (2013.01); *G01V 9/02* (2013.01); *G01V 11/00* (2013.01); *G01S 13/867* (2013.01); *G01S 13/9076* (2019.05); *G01V 8/005* (2013.01); *Y02A 90/32* (2018.01); *Y02A 90/344* (2018.01); *Y02A 90/36* (2018.01)

(58) Field of Classification Search
USPC ........ 73/152.54; 324/637; 702/6, 19, 34, 51, 702/35, 40, 181
See application file for complete search history.

(56) References Cited

U.S. PATENT DOCUMENTS

| | | | |
|---|---|---|---|
| 4,044,353 A | 8/1977 | Levy | |
| 4,210,023 A | 7/1980 | Sakamoto et al. | |
| 4,381,544 A | 4/1983 | Stamm | |
| 4,744,040 A | 5/1988 | Kawata et al. | |
| 5,321,408 A | 6/1994 | Jean et al. | |
| 5,365,178 A | 11/1994 | Van Der Pol | |
| 5,557,277 A * | 9/1996 | Tricoles ................. | G01S 13/36 324/326 |
| 5,847,567 A | 12/1998 | Kielb et al. | |
| 6,915,689 B2 | 7/2005 | Edvardsson | |
| 7,298,869 B1 * | 11/2007 | Abernathy ........... | G06K 9/0063 324/323 |
| 7,508,520 B1 * | 3/2009 | Lines ................. | G01N 21/3504 250/338.5 |
| 8,096,355 B2 | 1/2012 | McDaniel et al. | |
| 8,106,814 B2 | 1/2012 | Durand et al. | |
| 8,854,253 B2 | 10/2014 | Edvardsson | |
| 9,057,792 B2 | 6/2015 | Abrahamson | |
| 9,285,475 B1 | 3/2016 | Guy et al. | |
| 2002/0036814 A1 | 3/2002 | Mueller et al. | |
| 2004/0099058 A1 | 5/2004 | Edvardson | |
| 2005/0093548 A1 * | 5/2005 | Ueda .................... | G01N 27/043 324/357 |
| 2007/0090989 A1 | 4/2007 | Weil | |
| 2009/0024026 A9 | 1/2009 | Simpkin | |
| 2010/0171649 A1 | 7/2010 | Durand et al. | |
| 2012/0262326 A1 | 10/2012 | Abrahamson | |
| 2013/0332115 A1 * | 12/2013 | Pratt ...................... | G01N 22/04 702/190 |
| 2014/0284465 A1 | 9/2014 | Pottorf et al. | |
| 2016/0187524 A1 | 6/2016 | Suhami | |
| 2016/0282463 A1 | 9/2016 | Guy et al. | |

FOREIGN PATENT DOCUMENTS

| | | |
|---|---|---|
| CN | 103765246 | 4/2014 |
| CN | 103792586 | 5/2014 |
| CN | 104375202 | 2/2015 |
| EP | 2538192 | 12/2012 |
| JP | 2010025919 | 2/2010 |
| RU | 2291344 | 1/2007 |
| WO | WO2001/096818 | 12/2001 |
| WO | WO 2016/151579 | 9/2016 |

OTHER PUBLICATIONS

European Search Report of EP Application No. EP 16767871 dated Jul. 17, 2017.
Sternberg et al., "Mapping potential shallow groundwater in the Gobi Desert using remote sensing: Lake Ulaan Nuur", Journal of Arid Environments, vol. 118, pp. 21-27, Mar. 6, 2015.
Paloscia et al., "A Comparison of Algorithms for Retrieving Soil Moisture from ENVISAT/ASAR Images", IEEE Transactions on Geoscience and Remote Sensing, IEEE Service Center, Piscataway, NJ, US, vol. 46, No. 10, pp. 3274-3284, Oct. 1, 2008.
Salwa Farouk Elbeih, "An overview of integrated remote sensing and GIS for groundwater mapping in Egypt", Ain Shams Engineering Journal, vol. 6, No. 1, pp. 1-15, Oct. 8, 2014, Amsterdam, NL.
Paillou et al., "Mapping of a major paleodrainge system in eastern Libya using orbital imaging radar: The Kufrah River", Earth and Planetary Science Letters, North Holland Publ., Co., NL, vol. 277, No. 3-4, pp. 327-333, Jan. 30, 2009.
Mattia et al., "Hydrology and Earth Systems Sciences Soil moisture retrieval through a merging of multi-temporal L-band SAR data and Hydrologic modelling", Hydrology and Earth System Sciences, vol. 13, pp. 343-356, Jan. 1, 2009.
Mitchell et al., "Towards an operational SAR monitoring system for monitoring environmental flows in the macquarie Marshes", Wetlands Ecology and Management, Springer Netherlands, Dordrecht, vol. 23, No. 1, pp. 61-77, Jun. 25, 2014.
"Field Estimation of Soil Water Content: A Practical Guide of Methods", Instrumentation and Sensor Technology, IAEA, Vienna, 2005.
Sano et al., "Relation between ERS-1 Synthetic aperture radar data and measurements of surface roughness and moisture content of rocky soils in a semiarid rangeland", Water Resources Research, vol. 34, No. 6, pp. 1491-1498, Jun. 1998.
Wang et al., "Estimation of Surface Soil Moisture and roughness from multi-angular ASAR imagery in the Watershed Allied Telemetry Exprimental Research (WATER)", Hydrol. Earth Syst. Sci., 15, 1415-1426, 2011.
Komarov et al., "Permittivity and Measurements", Encyclopedia of RF and Microwave Engineering, p. 3693-3711, 2005.
Sternberg et al., "Mapping potential shallow groundwater in the Gobi Desert using remote sensing: Lake Ulaan Nuur", Journal of Arid Environments, vol. 118, pp. 21-27, 2015.
Paloscia et al, "A Comparison of Algorithms for Retrieving Soil Moisture from ENVISAT/ASAR Images", IEEE Transactions on Geoscience and Remote Sensing, IEEE Service Center, Piscataway, NJ, US, vol. 46, No. 10, Oct. 1, 2008, pp. 3274-3284.
Salwa Farouk Elbeih, "An overview of integrated remote sensing and GIS for groundwater mapping in Egypt", Ain Shams Engineering Journal, vol. 6, No. 1, Oct. 8, 2014, pp. 1-15.
Paillou et al., "Mapping of a major paleodrainage system in eastern Libya using orbital imaging radar: The Kufrah River", Earth and Planetary Science Letters, North Holland Publ., Co, NL, vol. 277, No. 3-4, Jan. 30, 2009, pp. 327-333.
Mattia et al., "Hydrology and Earth System Sciences Soil Moisture Retrieval Through a Merging of Multi-temporal L-band SAR data and hydrologic modelling", Hydrology and Earth System Sciences, vol. 13, Jan. 1, 2009, pp. 343-356.
Mitchell et al., "Towards an operational SAR monitoring system for monitoring environmental flows in the Macquarie Marshes", Wesrlands Ecology and Management, Springer Netherlands, Dordrecht, vol. 23, No. 1, Jun. 25, 2014, pp. 61-77.
European Search Report of Application No. EP 18174136 dated Sep. 24, 2018.
Chinese Office Action of Application No. 2016800047240 dated Nov. 6, 2018.
European Search Report of Application No. EP 18157509.3 dated Jul. 19, 2018.
Francois Jonard, "Soil water content estimation using ground-based active and passive microwave remote sensing: Ground-penetrating radar and radiometer", Universite catholique de Louvain, Aug. 2012, pp. 1-195.

(56) References Cited

OTHER PUBLICATIONS

J P Walker et al., "High resolution soil moisture mapping", Proceedings of the Fifth Global Workshop on Digital Soil Mapping, Jan. 1, 2012, pp. 45-51.

* cited by examiner

SYSTEM AND METHOD OF DETECTING UNDERGROUND GAS LEAKAGE

CROSS REFERENCE TO RELATED APPLICATIONS

This application is a continuation-in-part of U.S. patent application Ser. No. 15/014,053, filed on Feb. 3, 2016 and entitled SYSTEM AND METHOD OF UNDERGROUND WATER DETECTION which is a continuation in part of U.S. patent application Ser. No. 14/666,648, filed on Mar. 24, 2015, Now U.S. Pat. No. 9,285,475 and entitled SYSTEM AND METHOD OF UNDERGROUND WATER DETECTION, which are incorporated in their entirety herein by reference

FIELD OF THE INVENTION

The present invention relates generally to remote detection of underground gas leakage. More specifically, the present invention relates to systems and methods for remote detection of underground gas leakage using microwave radiation.

BACKGROUND OF THE INVENTION

Shortages in drinking water supplies is an acute global problem. Some shortages are caused by extensive leakage of drinking water from water supply systems. Water leakage can cause over 20-30% and even over 50% of the losses of drinking water in a typical urban water system. The older the water system the higher the chance for water leakage. Most water leakages occur underground and are hard to detect. Such underground leakages may only be detected only after causing above the ground floods or damage to buildings, infrastructure and the like.

There is no good current solution for detecting underground water leakages. An inspector can use a primitive device placing it above a place where he suspects an underground leakage exists, and attempting to identify water leakage sounds. Another way is to conduct a local excavation at the suspected area. However, local excavations are expensive, and may require the use of extensive algorithms which require pre-obtained data from the area of inspection and from the local authorities (such as municipalities).

Natural gas usually contains 98% $CH_4$, 1.16% higher hydrocarbons, 0.05% $CO_2$, 0.79% $N_2$ and 0.20 mg/m$^3$ S. Natural gas, like water, is transported underground with a ramified network of pipes, in many cases in very rural areas. In most cases the accessibility to these areas is very limited which results in poor ability to inspect the conditions and conduct maintenance of the pipes to an acceptable level according to the maintenance manuals. Gas leaks may happen due to faults (e.g., cracks) in the pipes, usually due to aging of the materials constructing the pipes or due to mechanical damage caused by an external force such as tree roots, ground movements and the like.

There is no good current solution for detecting underground gas leakages. Currently, an inspector has to walk over the underground pipe line while using his smell sense or a probe in order to detect small residuals of methane in the atmosphere. This method is unreliable and slow. A fast and reliable solution is needed.

SUMMARY OF THE INVENTION

Some embodiments of the invention are directed to a system and a method of determining underground liquid (e.g., water) or fluid content. Embodiments may include for example receiving a first scan of an area at a first polarization, the first scan including first L band microwave reflections from the area, receiving a second scan of the area at a second polarization, the second scan including second L band microwave reflections from the area, the first and second scans being from a first sensor for detecting L band microwave radiation reflections attached to an object located at least 50 meters ("m"), 70 m, 100 m or more, above the area and filtering electromagnetic noise from the first scan using the second scan. Embodiments of may include creating a water roughness map based on typical roughness values of various types of water sources and the filtered first scan, identifying a first type of water sources using the water roughness map and the filtered first scan and calculating the water content at locations in the area based on the identified first type of water sources.

Some embodiments of the invention include a method of determining underground liquid (e.g., water) content. Embodiments may include receiving a first scan of an area at a first polarization, the first scan including first L band microwave reflections from the area, the first scan being from a first sensor for detecting L band microwave radiation reflections, the first sensor attached to an object located at least 50 meters ("m"), 70 m, 100 m or more, above the area. Embodiments may include receiving optical data of or representing at least a portion of the scanned area. According to some embodiments, the optical data may be captured in a wavelength in a range between 1 millimeter to 10 nanometers (e.g., from infrared to ultraviolet). According to some embodiments electromagnetic noise from the first scan may be filtered using the optical data. Embodiments may include creating a water roughness map based on typical roughness values of various types of water sources and the filtered first scan, identifying a first type of water sources using the water roughness map and the filtered first scan and calculating the water content at locations in the area based on the identified first type of water sources.

Embodiments of the invention may detect underground gas leakage. Embodiments may include receiving a first scan of an area including an underground gas pipe at a first polarization, the first scan including first microwave reflections of the area at a wavelength range of 3.8 cm to 1.3 m, such that the first scan is from a first sensor for detecting microwave radiation reflections at a wavelength range of 3.8 cm to 1.3 m and the sensor may be located at least 50 meters above the area. Some embodiments may include receiving additional data, filtering electromagnetic noise from the first scan using the additional data and creating a water roughness map based on typical roughness values of a set of types of water sources and the filtered first scan. Some embodiments may include identifying one or more water accumulations at one or more locations along the gas pipe using the water roughness map and the filtered first scan and calculating the water content at the one or more locations along the gas pipe based on the identified one or more water accumulations. Some embodiments may include estimating based on the calculated water content one or more discharge rates of gas leaked from the gas pipe at the one or more locations along the gas pipe.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
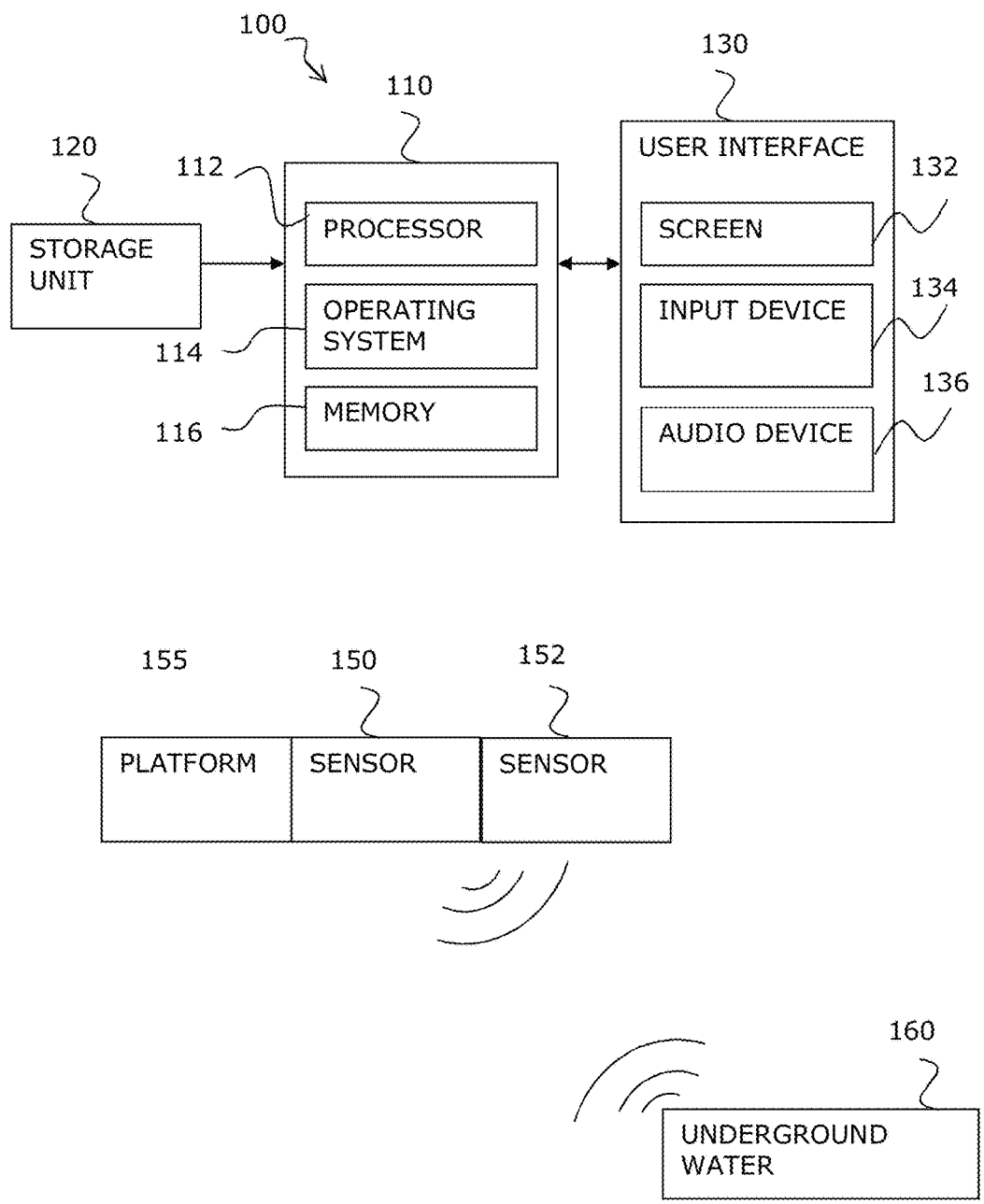
FIG. 1 is high level block diagram of an exemplary system for detecting underground water and/or detecting underground gas leakage according to some embodiments of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory processor-readable storage medium that may store instructions, which when executed by the processor, cause the processor to perform operations and/or processes as discussed herein. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. The term set when used herein may include one or more items. Unless explicitly stated, the method embodiments described herein are not constrained to a particular order or sequence. Additionally, some of the described method embodiments or elements thereof may occur or be performed simultaneously, at the same point in time, or concurrently.

Some embodiments of the invention are related to a method and a system for remote detection of underground water, for example, drinking water leakage from an urban water system. Water sources such as water pipes, lakes, swimming pools or the like reflect electromagnetic (EM) waves, both underground and above ground level. Water sources may reflect back microwaves in a wavelength range of 3.8 cm to 1.3 m, for example, at L band and/or P band frequencies. Every water source has typical reflections and typical EM behavior, the type of the water source may be identified using these typical reflections. EM sensors placed on an elevated platform for example, a satellite, an aircraft, an air balloon or the like, may send EM waves at a known frequency (e.g., 1.3 GHz) towards an area and read the EM waves reflected back from that area. The sensor may send a scan that includes all the reflections detected from a particular area to further be processed by a system according to some embodiments of the invention. The sensor may include Synthetic-Aperture Radar (SAR) SAR which uses a motion of a SAR antenna over a target region to provide finer spatial resolution than is possible with conventional beam-scanning radars. The scan may include all the EM reflections received from the area. These reflections may include both reflections from water sources and undesired reflections from other bodies in the area, such as buildings, vegetation and other topographical feature of the area. In order to identify the water related reflections, the undesired reflections (e.g., EM noise reflection) may be filtered or removed from the scan. In order to reduce (e.g., remove or filter) the EM noise two or more scans may be taken from the area at two different polarizations, for example, a horizontal-vertical (HV) scan and horizontal-horizontal (HH) scan. The HH reflections may be received from transmitting waves having a horizontal polarization that were received at horizontal modulation. The HV reflections may be received from transmitting waves having a horizontal polarization that were received at vertical modulation.

Some embodiments of the invention may transmit and receive reflections having two different resolutions. For example, HH and HV scans may be received from a first sensor having a first resolution and an additional HH (and/or HV) scan may be received from a second sensor, such that the second sensor has a higher resolution (e.g., 6 m$^3$) than the resolution of the first sensor (e.g., 12 m$^3$). The scans from the first sensor may be used to identify the EM noise reflections and to filter them from (e.g., remove them from) the scan received from the second sensor. In some embodiments, all the scans may be received from a single sensor having a high resolution (e.g., 6 m$^3$, 3 m$^3$). Two HH and HV scans may be received from a single sensor and may include all the information required for filtering (e.g., reducing) the EM noise and receiving a scan having a sufficient resolution. In some embodiments, additional scans having additional polarizations may be received from the single sensor all in the same resolution. Such additional scans may allow further reduction of the EM noise.

After the filtration of the EM noise at least some of the scanned reflections may be identified as water reflections. Since different water sources (e.g., drinking water, sewage, seas, lakes swimming pools, etc.) have different typical EM roughness (typical EM reflections), it may be possible to distinguish one from the other. In some embodiments, EM roughness from sewage pipes, seas, lakes and swimming pools may be filtered or removed from the filtered noise scan thus leaving in the scan only reflection received from water leakages. Since the resolution (e.g., at least 3 m$^3$) of the scan is larger than the diameter of the pipes only a leakage larger than this resolution may be detected and not the pipes themselves.

In some embodiments, a drinking water content or amount may be calculated from the drinking water related reflections and converted into quantities of water capacity (e.g., cubic meters/hour, gallons/hour, etc.,). This information may be displayed on a geographical map (e.g., a street map of a city) showing, for example, the amount and location of each suspected leakage in a city.

Reference is now made to FIG. 1 which is high level block diagram of an exemplary system for remote detecting underground water according to some embodiments of the invention. A system 100 may include a computer processing device 110, a storage unit 120 and a user interface 130. System 100 may receive from a sensor 150 microwave scans at a wavelength range of 3.8 cm to 1.3 m (e.g., in an L band and/or in a P band) from an area that includes at least one underground water source 160. Processing unit 110 may include a processor 112 that may be, for example, a central processing unit (CPU), a chip or any suitable computing or computational device, an operating system 114 and a memory 116. System 100 may be included in a desktop computer, laptop commuter, a tablet, a mainframe computer or the like. Processor 112 or other processors may be configured to carry out methods according to embodiments of the present invention by for example executing instructions stored in a memory such as memory 116. In some embodiments, system 100 may further receive form a second sensor 152 microwave scans at a wavelength range of 3.8 cm to 1.3 m (e.g., in L and/or P bands) from an area that includes at least one underground water source 160.

Operating system 114 may be or may include any code segment designed and/or configured to perform tasks involving coordination, scheduling, arbitration, supervising, controlling or otherwise managing operation of processing device 110, for example, scheduling execution of programs. Operating system 114 may be a commercial operating system. Memory 116 may be or may include, for example, a Random Access Memory (RAM), a read only memory (ROM), a Dynamic RAM (DRAM), a Synchronous DRAM (SD-RAM), a double data rate (DDR) memory chip, a Flash memory, a volatile memory, a non-volatile memory, a cache memory, a buffer, a short term memory unit, a long term memory unit, or other suitable memory units or storage units. Memory 116 may be or may include a plurality of, possibly different memory units.

Memory 116 may store any executable code, e.g., an application, a program, a process, operations, task or script. The executable code may when executed by a processor cause the processor to detect underground water and perform methods according to embodiments of the present invention. The executable code may be executed by processor 112 possibly under control of operating system 114. Memory 116 may store data such as for example images, gray scale or intensity levels, scans, reflections, etc.

Storage 120 may be or may include, for example, a hard disk drive, a floppy disk drive, a Compact Disk (CD) drive, a CD-Recordable (CD-R) drive, a universal serial bus (USB) device or other suitable removable and/or fixed storage unit. Content may be stored in storage 120 and may be loaded from storage 120 into memory 116 where it may be processed by processor 112. For example, storage 120 may include scans of microwaves in a wavelength range of 3.8 cm to 1.3 m of areas at various polarizations received from sensor 150, geographical data related to the scanned area (e.g., a type of soil, amount of humidity in the solid, a road map, etc.), and roughness values of various types of water sources or any other required data according to embodiments of the invention.

User interface 130 may be, be displayed on, or may include a screen 132 (e.g., a monitor, a display, a CRT, etc.), an input device 134 and an audio device 136. Input device 134 may be a keyboard, a mouse, a touch screen or a pad or any other suitable device that allows a user to communicate with processor 112. Screen 132 may be any screen suitable for displaying maps and/or scans according to embodiments of the invention. In some embodiments, screen 132 and input device 134 may be included in a single device, for example, a touch screen. It will be recognized that any suitable number of input devices may be included in user interface 130. User interface 130 may include audio device 136 such as one or more speakers, earphones and/or any other suitable audio devices. It will be recognized that any suitable number of output devices may be included in user interface 130. Any applicable input/output (I/O) devices may be connected to processing unit 110. For example, a wired or wireless network interface card (NIC), a modem, printer or facsimile machine, a universal serial bus (USB) device or external hard drive may be included in user interface 130.

Embodiments of the invention may include an article such as a computer or processor non-transitory readable medium, or a computer or processor non-transitory storage medium, such as for example a memory, a disk drive, or a USB flash memory, encoding, including or storing instructions, e.g., computer-executable instructions, which, when executed by a processor or controller, carry out methods disclosed herein. The storage medium may include, but is not limited to, any type of disk including floppy disks, optical disks, compact disk read-only memories (CD-ROMs), rewritable compact disk (CD-RWs), and magneto-optical disks, semiconductor devices such as read-only memories (ROMs), random access memories (RAMs), such as a dynamic RAM (DRAM), erasable programmable read-only memories (EPROMs), flash memories, electrically erasable programmable read-only memories (EEPROMs), magnetic or optical cards, or any type of media suitable for storing electronic instructions, including programmable storage unit.

A system 100 may include or may be, for example, a personal computer, a desktop computer, a mobile computer, a laptop computer, a notebook computer, a terminal, a workstation, a server computer, a tablet computer, a network device, or any other suitable computing device. Unless explicitly stated, the method embodiments described herein are not constrained to a particular order or sequence. Additionally, some of the described method embodiments or elements thereof can occur or be performed at the same point in time.

Sensor 150 and/or sensor 152 may be any sensor that is configured to scan and detect underground water, such as underground water source 160 using electromagnetic radiation. For example, sensor 150 may include a receiver for a radar or Synthetic-Aperture radar (SAR) SAR. Sensors 150 and/or 152 may be located at least 50 meters above the above the ground. Sensors 150 and/or 152 may be placed for example on an elevated platform or structure 155. Elevated platform or structure 155, may be for example, a satellite, an aircraft or an air balloon and may be located at least 50 meters above the ground (e.g., at an elevation of 50 m), for example, 70 meters, 100 meters, 150 meters, 500 meters, 1000 meters or more. Sensor 152 may have different detection resolution (e.g., higher resolution) than sensor 150.

Figure 2:
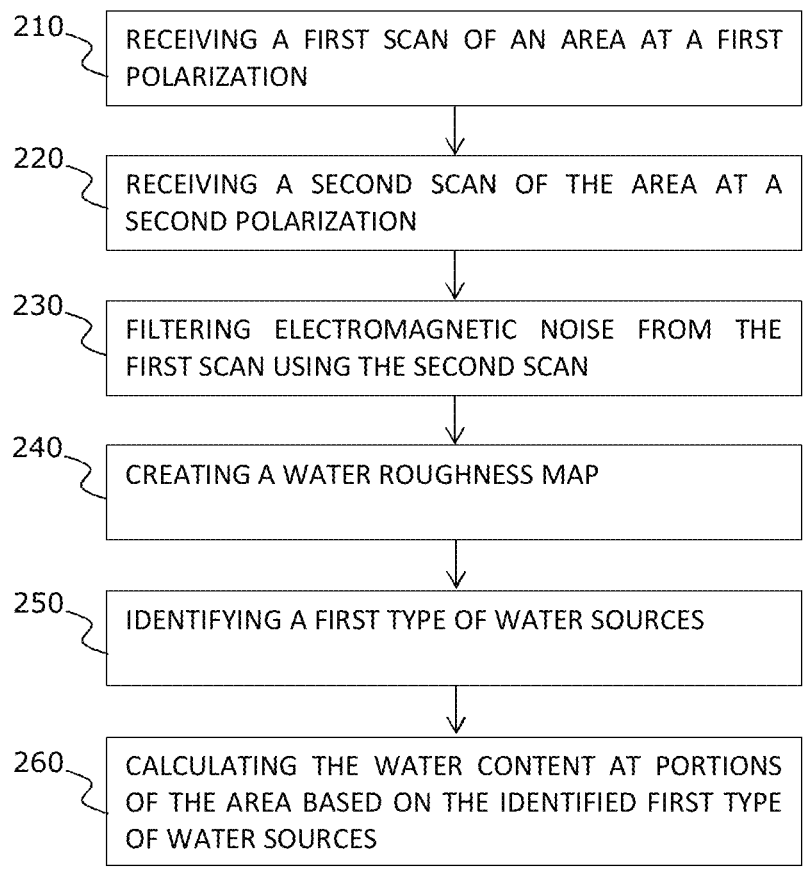
FIG. 2 is a flowchart of an exemplary method of detecting underground water according to some embodiments of the invention.

Reference is made to FIG. 2, a flowchart of an exemplary method of remote detecting underground water according to some embodiments of the invention. Embodiments of the method of FIG. 2 may be performed for example by system 100 or by another system. In operation 210, a first scan of an area at a first polarization may be received. The first scan may be a two-dimensional scan of an area. The first scan may include a first microwave reflections from the area at a wavelength range of 3.8 cm to 1.3 m, for example, L band and/or P band reflections. The first scan may include reflections received from a predefined area on the ground, converted into data, e.g., data including pixel data. The size of each pixel may depend on the resolution of a sensor (e.g., sensor 150, 152) located at least 50 meters above the ground. The sensor may receive reflection from both above ground and underground objects. A processor associated with the sensor may convert these reflections into data including pixels having different gray-levels. This data may be received and analyzed by system 100. The size of the area scanned is determined by the sensor (e.g., a SAR sensor) and may be received as raw data. The gray scale level of each pixel converted from microwave reflection of the scan may be related to a reflection intensity level received from a single area unit (e.g., 3 m$^2$) at a respective depth (e.g., 3 m). For example, a pixel may be related to reflections received from 2 m$^3$, 3 m$^3$, 6 m$^3$, 12 m$^3$, or the like.

L band microwave reflections, P band microwave reflection, other microwave reflections (e.g., at a wavelength range of 3.8 cm to 1.3 m) or other radiofrequency (RF) wave reflections may be received from a sensor for detecting L band and/or P band microwave or RF radiation reflections (e.g., sensor 150 or 152). L band microwaves may include for example radiofrequency waves in a frequency range of 1-2 GHz (a wavelength range of 30-15 cm) and P band microwaves may include radiofrequency waves in a frequency range of 0.999 to 0.2998 GHz (a wavelength range of 30-100 cm). The sensor may be located coextensively, near or on, or may be attached to, an object (e.g., platform 155) located at least 50, 100 meters, 1000 meters or more above the area. Such a sensor may be attached to an elevated platform, for example, a satellite, an aircraft or an air-balloon. Microwaves at a wavelength range of 3.8 cm to 1.3 m, for example, at L band and/or at P band reflections or other RF waves may be transmitted from a transmitter towards the scanned area and reflected back from the scanned area after interacting with objects both above the ground and under the ground. The penetration depth of the microwaves into the ground may vary with the type of the soil, the amount of moisture in the soil, the structure of the land cover or the like. Exemplary penetration depth may be between soil surface to 3 meters depth from a remote sensor located at least 50 meters above soil surface. The microwaves reflected back from the scanned area may be received and detected by the sensor. The sensor may identify reflections having different polarizations. Sensors 150 and 152 may each be configured to detect reflections having different resolution, for example, the sensors may be used for receiving scans at resolutions of 6 m$^3$ and 12 m$^3$.

The microwaves at a wavelength range of 3.8 cm to 1.3 m, or other RF waves may be transmitted in a first polarization, for example, a horizontal polarization or a vertical polarization and the sensor may detect reflections having various modulations. For example, reflections from waves that were transmitted at horizontal polarization may be detected at vertical modulation (HV polarization) or may be detected at horizontal modulation (HH polarization). Other polarizations may include vertical-vertical (VV) polarization and vertical-horizontal (VH) polarization.

In operation 220, a second scan of the area at a second polarization may be received. The second scan may include second microwave reflections from the same area at a wavelength range of 3.8 cm to 1.3 m, for example, L band and/or P band reflections. In some embodiments, if the first polarization is an HV polarization, than the second polarization may be HH polarization. In some embodiments, the second polarization may be VH polarization or VV polarization. Some embodiments may include receiving a third scan of the area at a second polarization (e.g., HH polarization), the third scan including third microwave reflections from the area, at a wavelength range of 3.8 cm to 1.3 m, for example, L band and/or P band reflections, at a higher resolution than that of the first and second scans. For example, if the first and second scans are received from a first sensor, at a resolution of 12 m$^3$, the third scan may be received, from a second sensor for detecting the microwave radiation reflections, at a resolution of 6 m$^3$. The second sensor may be located or may be attached to an object (e.g., a satellite, an airplane or an air-bloom) located at least 50 meters, 100 meters, 1000 meters or more above the area, calibrated similarly to the first sensor, such that a gray level of a pixel converted from an intensity level of microwave reflections in the first and second scans received from a specific location in the area may have corresponding gray level of a pixel (or pixels) converted from an intensity level of microwave reflections in the third scan received from that specific location. For example, if the first and second scans have a resolution of 12 m$^3$ (or 13×6 m$^2$) for every pixel in the first and second scans 4 corresponding pixels (or 2 corresponding pixels) may be received in the third scan. Other numbers of scans may be used.

Figure 3A:
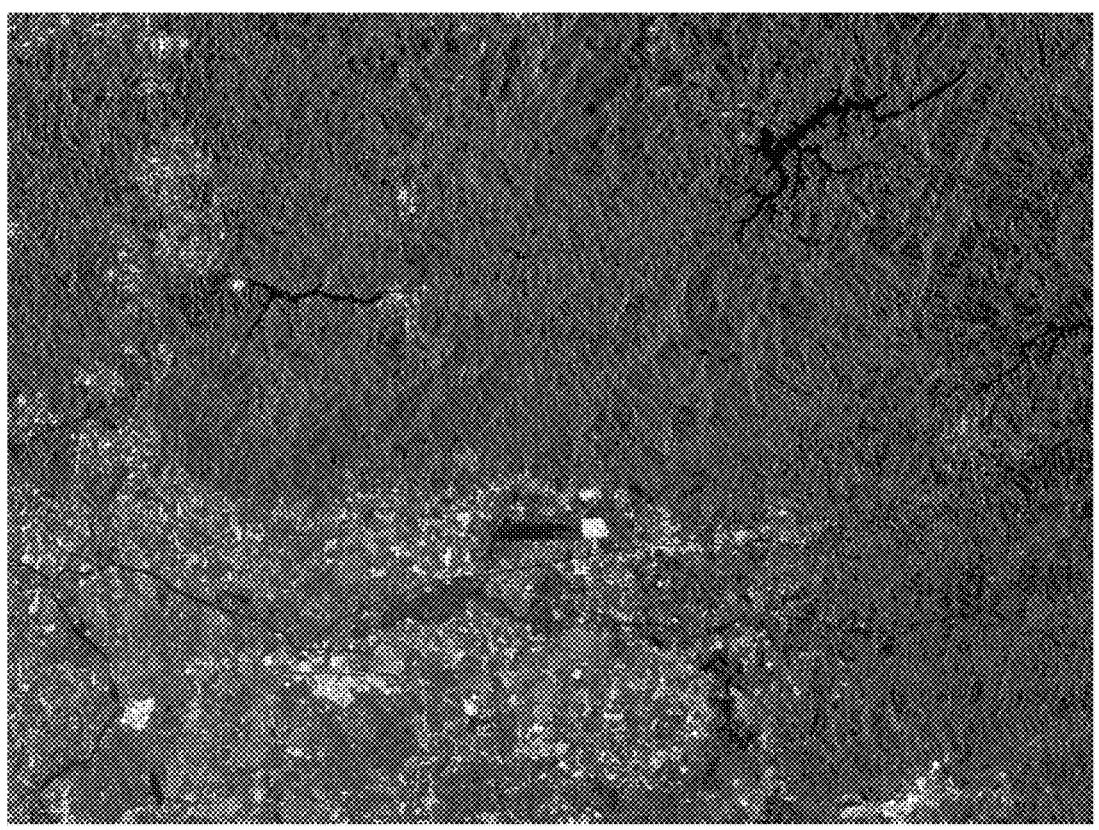
FIGS. 3A-3B are exemplary scans of L band microwave reflections from the area a horizontal-vertical (HV) and horizontal-horizontal (HH) polarizations according to some embodiments of the invention.
Figure 3B:
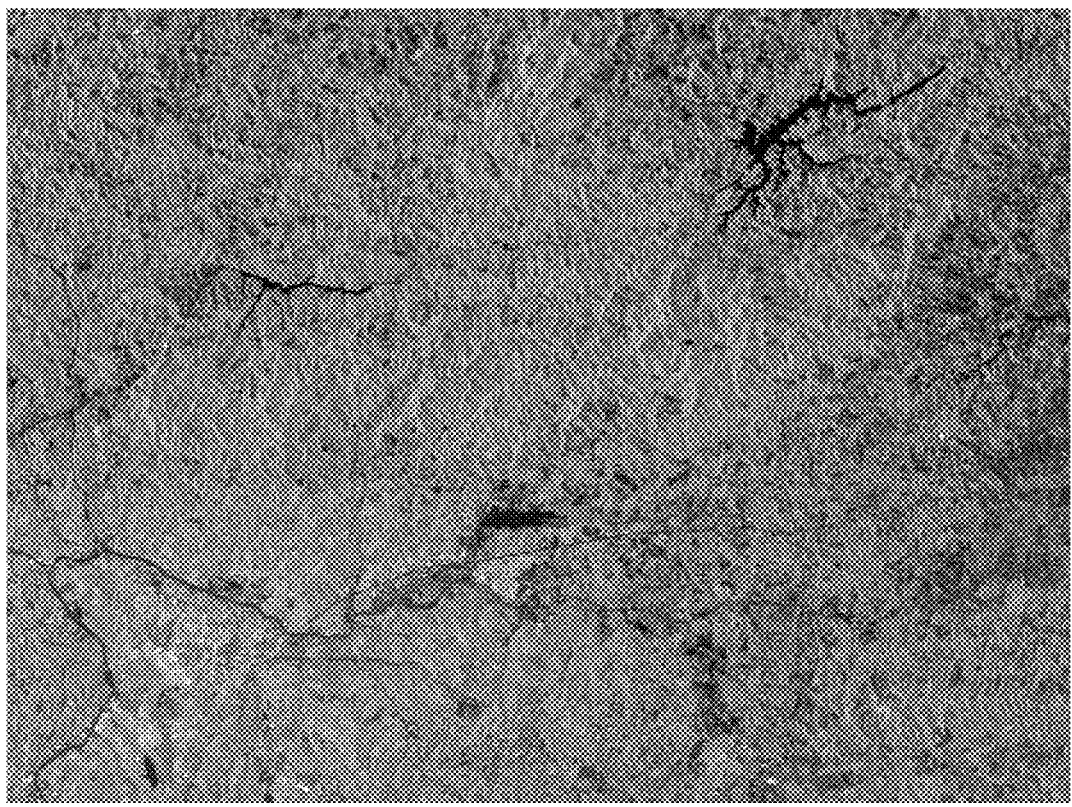

The first, second and optionally the third scans may be received as grayscale images of microwave intensity levels converted into grayscale levels (e.g. each pixel in the map has different gray level). Exemplary scans received at a resolution of 12 m$^3$ are given in FIGS. 3A and 3B. FIGS. 3A and 3B are exemplary scans taken above an urban area in Oakland, Calif., as received from an L-band microwave sensor (e.g., a SAR) located on a satellite. FIG. 3A is a scan having a HV polarization and FIG. 3B is a scan having a HH polarization. In some embodiments, the first and second microwave reflections at a wavelength range of 3.8 cm to 1.3 m, from may be converted from gray scale levels to intensity levels. As used herein gray scale levels may be defined according to the ratio between black pigment or level and white pigment or level at each pixel. The gray levels may be correlated to microwave reflection intensity. The higher the amount of black level or pigment the higher is the intensity of the microwave reflection from a particular area (e.g., pixel). For example, the gray scale level data received from the sensor may be converted to Decibel (dB) intensity level, using for example, equation 1:

$$I_{dB} = 10 \cdot \log(DN^2) - 83 \quad (1)$$

wherein, $I_{dB}$ is the converted intensity level in each pixel and DN is the gray scale level in each pixel.

It should be understood by those skilled in the art, that equation 1 is given as an example only and converting gray levels to other intensity levels using different equations are within the scope of the invention. Some embodiments may include also converting the third scan from gray scale into intensity levels.

Some embodiments may include receiving a fourth scan of the area at a third polarization, the fourth scan including fourth microwave reflections from the area at a wavelength range of 3.8 cm to 1.3 m, for example, L band and/or P band reflections. For example, the fourth scan may include reflections having VH polarization. Some embodiments may include receiving a fifth scan of the area at a forth polarization, the fifth scan including fifth microwave reflections from the area at a wavelength range of 3.8 cm to 1.3 m, for example, L band and/or P band reflections. For example, the fourth scan may include reflections having VV polarization. The fourth and fifth scans may be received from the first sensor (e.g., a sensor having a resolution of 6 m³).

In some embodiments, all the received scans (e.g., first-fifth) may be converted from gray scale to intensity levels, using for example, equation (1).

In operation 230, electromagnetic (EM) noise may be filtered from the first scan using the second scan. The electromagnetic noises may include reflections reflected or bounced from buildings, vegetation or other topographical features located at the scanned area. There are several methods known in the art for filtering EM noise from EM and RF signals and the invention is not limited to a particular method or algorithm. Some exemplary methods for filtering EM noise, from each pixel, according to embodiments of the invention may include reducing noise from buildings using for example the following equations (as with other equations discussed herein, other or different equations may be used):

$$Fd = \tfrac{1}{2}(HR_{dB}^2 - 2 \cdot HV_{dB}^2) \quad (2)$$

wherein Fd is electromagnetic noise from bouncing reflection from solid objects located in the scanned area, $HH_{dB}$ is the intensity level of HH polarization reflection at that pixel, and $HV_{dB}$ is the intensity level of HV polarization reflection at that pixel. In some embodiments, filtering electromagnetic noise may include filtering reflection received from solid objects located in the scanned area.

$$C = (HH_{dB}^2)/(2Fd) \quad (3)$$

$$Fv = 2 \cdot (\tfrac{1}{2}HH_{dB}^2 - Fd \cdot C^2) \quad (4)$$

wherein Fv is the calculated electromagnetic reflection noise received from solid objects located in the scanned area.

In some embodiments, reflections from additional polarizations (e.g., VV and VH polarizations) may be used to filter the EM noise. For example, such reflections may be included in an extended equation (2). Various parameters such as Fv and C calculated in equations (2)-(4) may be used to calculate a filtered first scan, according to equation (5).

$$Bs = HH_{dB} - (\text{the EM noise}). \quad (5)$$

wherein Bs is filtered EM noise refection

Figure 4:
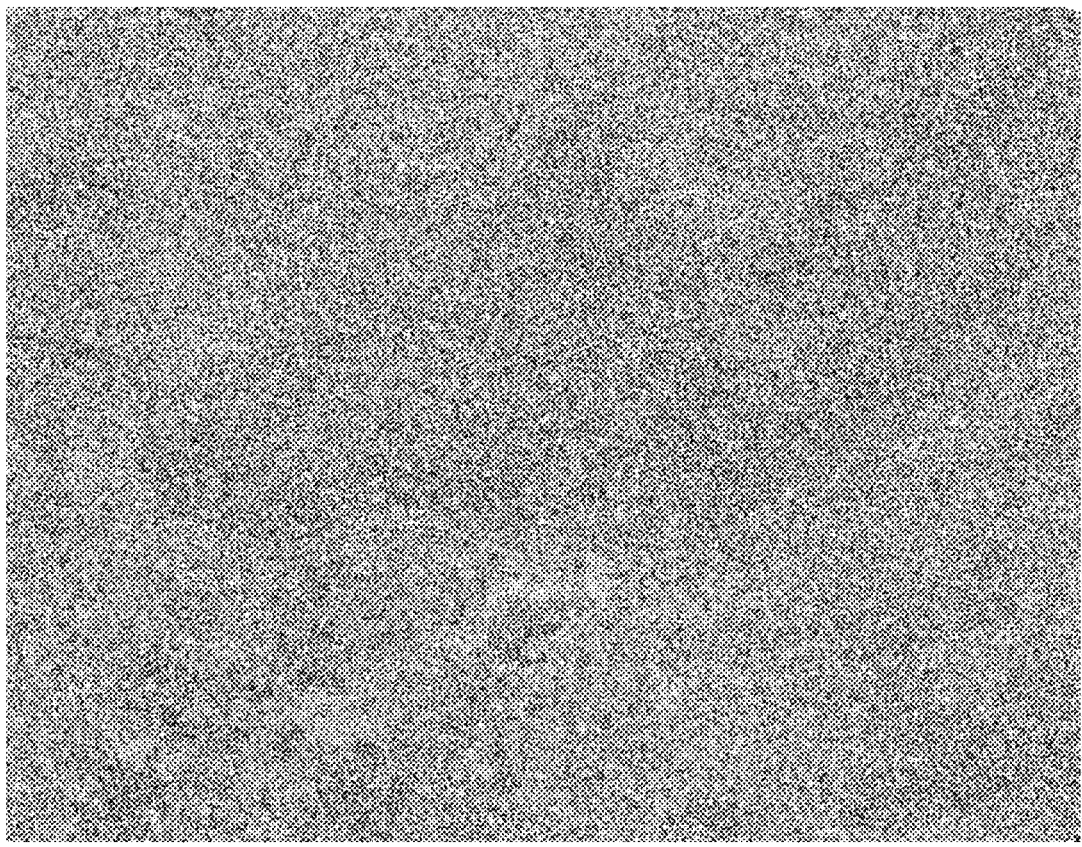
FIG. 4 is the exemplary HH polarized scan after filtering electromagnetic noise according to some embodiments of the invention.

An exemplary HH polarized scan (e.g., Bs scan) after filtering electromagnetic noise according to some embodiments of the invention is given in FIG. 4. As one can see in comparison to the scans in FIGS. 3A and 3B, the filtered scan is relatively homogeneous with no large noisy areas or portions. FIGS. 4-7 are gray scale representations of the intensity level at each pixel in the scans. FIGS. 4-7 were created by reconverting the intensity levels used for calculating the various steps of the method from dB to gray scale, using the invert equation of equation (1).

Figure 5:
FIG. 5 is an exemplary water roughness map according to some embodiments of the invention.

In operation 240, a water roughness map may be created based on typical roughness values of various (e.g., a set of) types of water sources and the filtered first scan. In some embodiments, typical roughness values of various types of water sources may be stored in a database associated with processor 112, for example, in storage unit 120. Different water sources such as, salty seas, lakes, rivers, swimming pools, sewage pipes and drinking water pipes have different typical reflections recorded and known from the art. This data may be used to create a water roughness map that includes all the undesired water sources, for example, the map may include mapping all reflections related to water sources other than drinking water (e.g., in urban areas sources like rivers, swimming pools and sewage pipes). An exemplary process of creating a water roughness map is given in equation (6).

$$Ks = aBs^2 + bBs + c \quad (6)$$

wherein: a is the average roughness of drinking water, b is the average roughness of open sweet water sources (e.g., swimming pools, fountains and lakes) and c is the average roughness of sewage water. An exemplary water roughness map is given in FIG. 5. FIG. 5 is mostly dark, the dark part is where no water roughness is detected.

In some embodiments, the water roughness may be calculated based on the chemical composition of the water. The amount of chemicals that may be solute in the water may affect the dielectric properties of the water. It is well known in the art that the amount of salinity may change the dielectric constant of the water, the higher the salinity the higher is the dielectric constant, for a given frequency. Underground water having different dielectric constants may have different water roughness (e.g., different typical microwave reflections) at the same conditions. Some exemplary solutes such as chlorine, calcium and bicarbonates may contribute to the salinity of the water. Drinking water at different areas on the globe has different salinity levels, for example, the amount of calcium in the drinking water in Israel is much higher than the amount of calcium in the drinking water in Germany In Israel the rocks and soil contain large amount of limestone which contributes to the amount of calcium in the water. In some areas there may be a difference in the chemical composition of the water even between two neighboring cities, due to fluorination of the water or other manipulations of the drinking water conducted by, for example, the local municipality.

In some embodiments, when the water roughness is calculated based on the chemical composition of the water, for example using equation (6) above, and may include selecting the "a" parameter and/or the "c" parameter of equation (6) based on the chemical composition of the water in the area. In some embodiments, selecting the "a" parameter may include selecting the parameters from a lookup table stored in a memory associated with processor 112, for example, in storage unit 120. The lookup table may include a list of various "a" and/or "c" parameters for water having various chemical compositions. Additionally or alternatively, selecting "a" parameter and/or "c" parameter may include modifying (e.g., by multiplying with a "salinity parameter") the "a" parameter and/or "c" parameter. The salinity parameter may be stored in a memory associated with processor 112, for example, in storage unit 120.

In operation 250, a first type of water source may be identified using the water roughness map and the filtered first scan. Exemplary equations (7) and (8) may be used for calculating value of the first water source.

$$Wc' = Bs \cdot Ks^{Ks} \tag{7}$$

$$Wc = -d \cdot Wc'^2 - e \cdot Wc' - f \tag{8}$$

wherein: Wc is the calculated value of the first water source (e.g., drinking water) in each pixel in the scanned area, d is a constant related to an urban area, e is a constant related to a semi-urban area and f is a constant related to a non-urban area. These constants may vary with the type of water source, the type of soil, the amount of moisture in the soil, precipitations (e.g., rain) in the area in a predetermined time interval prior to the calculation (e.g., a week), or the like.

In some embodiments, Wc may be calculated additionally using a correction parameter based on at least one of: the type of the soil at the area, the density of the soil at the area and a topography of the scanned area. In some embodiments, calculating Wc may include reducing a moisture level from the identified water sources received from a database. The moisture level may be calculated based on at least one of: moisture characteristics of a soil in the area and an amount of precipitations (e.g., rain) in the area in a predetermined time interval prior to the calculation (e.g., a week).

Figure 6:
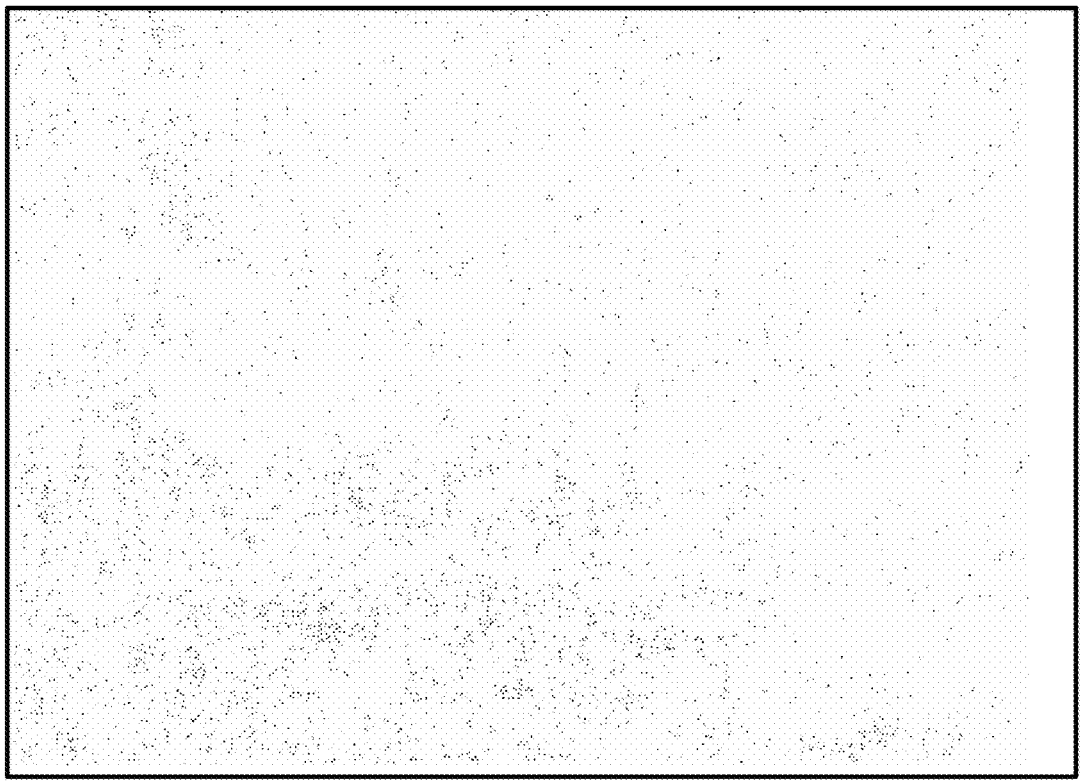
FIG. 6 is an exemplary map with identified drinking water sources according to some embodiments of the invention.

FIG. 6 is an exemplary map with identified water sources according to some embodiments of the invention, showing water content in a geographical representation. Since the detection resolution of the drinking water is equal to the resolution of the first, second and optionally third scans, drinking water or other water sources smaller than the scanned resolution (e.g., 3 $m^2$, 6 $m^2$, 12 $m^2$, or the like) cannot be detected.

Figure 7:
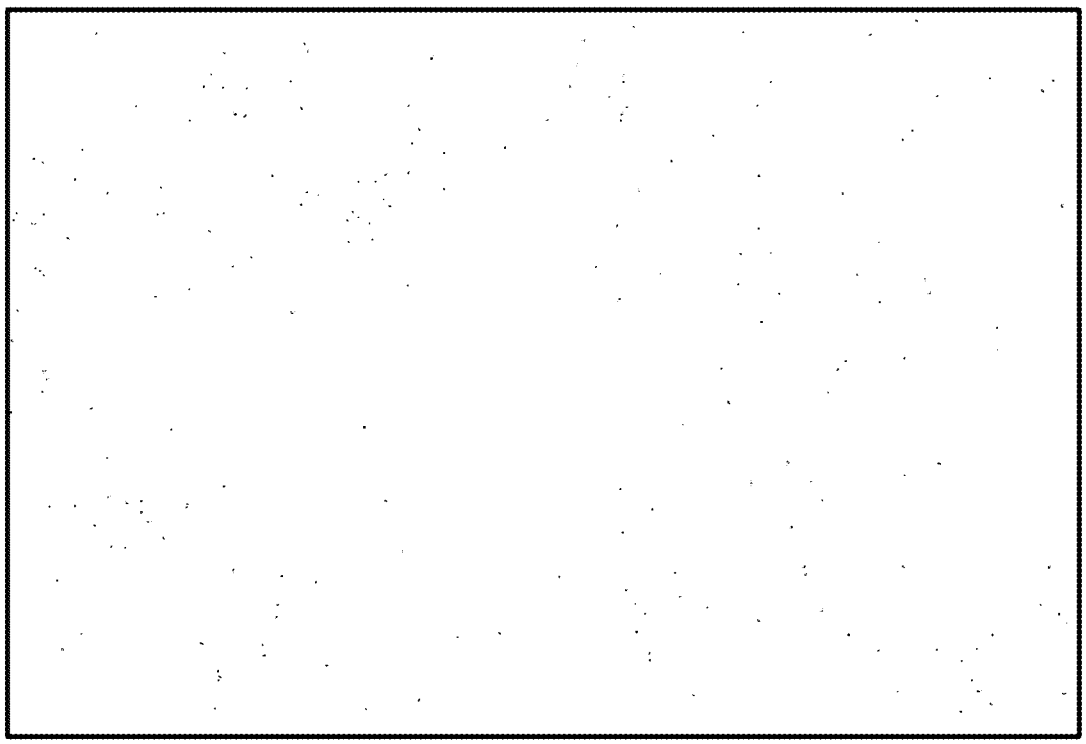
FIG. 7 is an exemplary map with identified drinking water leakages according to some embodiments of the invention.

FIG. 7 is an exemplary map with identified drinking water leakages (e.g., a Wc map) according to some embodiments of the invention. Each small dot on the map has different gray scale (e.g., different water content) and corresponds to water leakage. Some water leakages may be larger than areas covered by a single pixel and may include several pixels. Embodiments may include summing or combining together neighboring pixels identified as drinking water leakages to define a single leakage. The intensity levels may be calculated for example in dB values and may be converted to water capacity.

In operation 260, the water content may be calculated at different locations in the area based on the identified first type of water sources. In some embodiments, since every identified water source (e.g., leakage) has its own intensity value, these values may be used to calculate the water content related to each water source. The higher the intensity level (e.g., the higher the Wc at that pixel or the sum of Wc in neighboring pixels) the higher is the water content. Embodiments may include converting the calculated water content from reflection intensity levels to quantities of water capacity for the different area location, for example, in gallons per hour, cubes per hour, etc. The water capacity may be proportional to the intensity. Different constants may be used to convert the intensity levels to capacities as a function of the capacity unit used (e.g., gallons/hour, cubes/ hour, etc.) The calculated intensity level for each pixel may be multiplied by a known constant (e.g., different constants may be used for different capacity units) converting the intensity levels into water capacities. Some embodiments may include summing capacities calculated for neighboring pixels. Water capacities calculated for several neighboring pixels, each corresponding to a location in the scanned area, may indicate that a large underground water leakage may be found in the corresponding locations.

Figure 8:
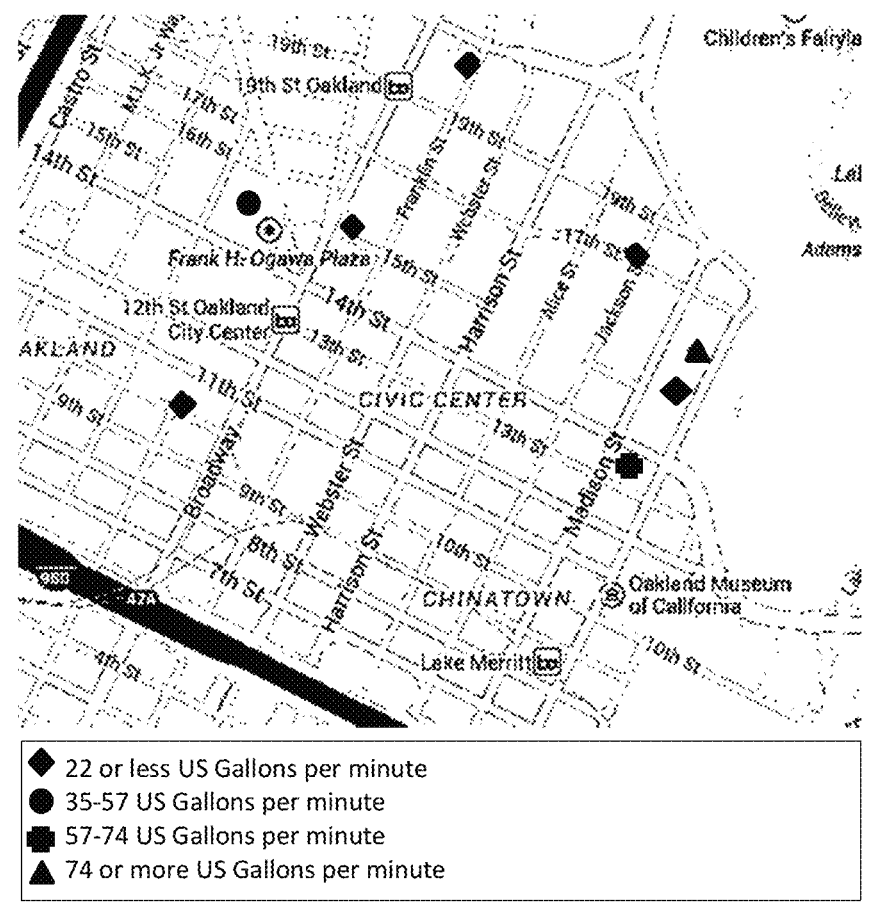
FIG. 8 is an exemplary graphical map showing the amount and location of water leakages according to some embodiment of the invention.

Some embodiments may include displaying the converted quantities of water capacity on a graphical map of the one or more scanned area. The converted quantities may be displayed on: a street map of an urban area, a road map of a county, satellite map, or the like. The converted quantities of water capacity may be displayed on screen 132 included in user interface 130. An exemplary street map of the Oakland, Calif. city center with locations of drinking water leakages is shown in FIG. 8. Since the received scans may include information (e.g., pixels) from a relatively large area, the geographical map presenting the data to a user (e.g., city official) may include only a portion of the scanned area. The user may shift the geographical map on the screen (e.g., using a mouse or a keyboard) covering all areas of interest (e.g., the city quarters) in the scanned area. Some of the detected leakages, illustrated as small gray dots in FIG. 7 were given a water capacity value and location in the corresponding geographical map (e.g., using coordinates). For example, as illustrated in FIG. 8 each of the marks located in a particular place on the map presents different amounts of water leakage (e.g. in gallons/hour). It should be appreciated by those skilled in the art that the displayed information may be displayed on top of a Geographic Information System (GIS). It should be further appreciated that additional information may be displayed alongside the water capacity value and location information, such as, water pipes, water valves and the like. Such a representation may allow better understanding of the source of a water leakage and may facilitate decision making in real time.

Figure 9:
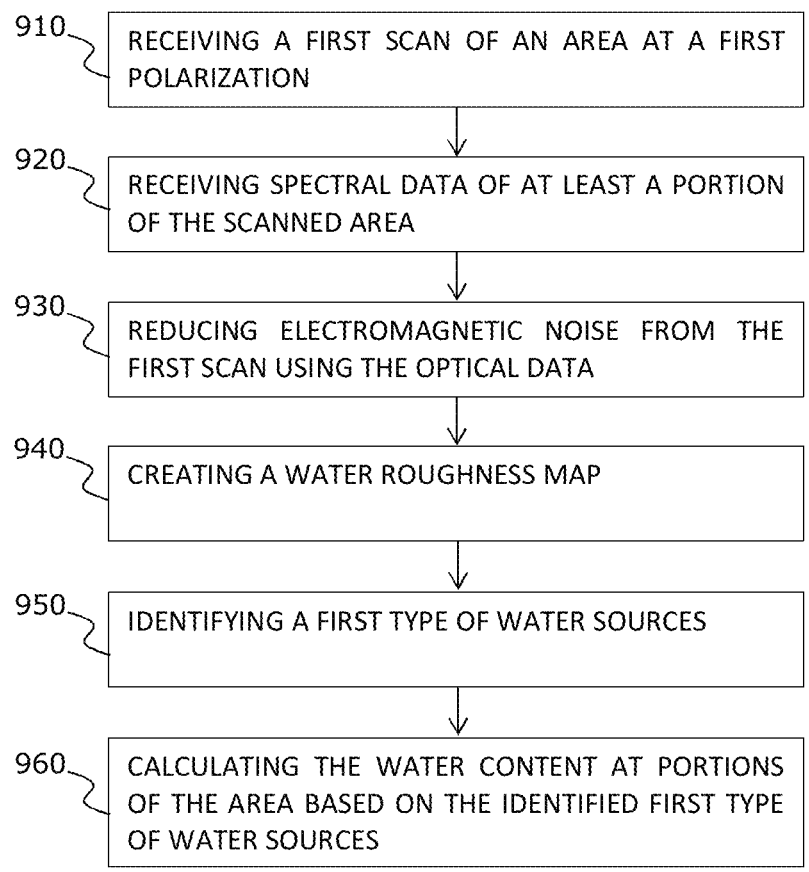
FIG. 9 is a flowchart of an exemplary method of detecting underground water according to some embodiments of the invention.

Reference is made to FIG. 9, a flowchart of an exemplary method of remote detecting of underground water according to some embodiments of the invention. Some embodiments may be performed, for example, by system 100 or by another system. In operation 910, a first scan of an area at a first polarization may be received. Operation 910 may be substantially the same as operation 210 of the method illustrated in FIG. 2 and may include the operations, steps and equations described above with respect to operation 210.

In operation 920, spectral data (e.g., optical data) of or representing at least a portion of the scanned area may be received. The spectral data may be captured in a wavelength in the range of 1 millimeter to 10 nanometers (e.g., from the infrared to the ultraviolet spectrum). The spectral data may be received from at least one capturing device or a sensor (such as sensor 150 or 152) located either on platform 155 or elsewhere. The capturing device may include an infrared (IR) camera, a visible light camera and/or an ultraviolet (UV) camera. The spectral data may include satellite-borne spectral imagery, airborne spectral imagery or the like. Exemplary spectral data may include an IR image of the area captured by an IR camera, a visible light photograph of the area (e.g., an aerial photograph) or a UV scan of the area.

In operation 930, electromagnetic noise may be filtered from the first scan using the spectral data. In some embodiments, the color (e.g., the wavelength) or intensity of neighboring pixels in the spectral data may be compared to detect differentiations or unexpected colors in the spectral data. For example, IR radiation may vary due to temperature differences at various locations in the scanned area. Underground water may cool down the temperature of the soil and land being wetted by the underground water leakage, in comparison to nearby soil and land. In some embodiments, a detection of an area cooler than nearby areas may indicate the presence of underground water. In yet another example, the presence of underground water may affect the presence of vegetation at certain areas and/or the color of the vegetation or soil. For example, the presence of underground water: may cause growth of significant lichen in between paving-stones in a flagging, may cause regeneration of green leaves in some of the vegetation in substantially dry vegetation (e.g., during the summer), may cause a change in the color of the soil (e.g., to become darker) or the like. These changes in the color, if detected, may indicate the presence of unground water. In some embodiments, the detected indication to a presence of underground water may be used to filter the EM noise from the first scan.

Some embodiments may include receiving a second scan of the area at a second polarization, where the second polarization may be the same or may be different from the first polarization. The second scan may include second microwave reflections from the area at a wavelength range of 3.8 cm to 1.3 m, for example, L band and/or P band reflections, the second scan being from the first sensor as discussed with respect to operation 220 of the embodiment illustrated in FIG. 2. In some embodiments, filtering the EM noise from the first scan may further include using the second scan, as discussed with respect to operation 230 of the embodiments of FIG. 2.

Operations 940-960 may be substantially the same as operations 240-260 of the embodiments of FIG. 2 and may include the steps, operations and equations of operations 240-260. The embodiment of FIG. 9 may include any operation or step that may be included and disclosed with respect to the embodiment of FIG. 2.

Figure 10:
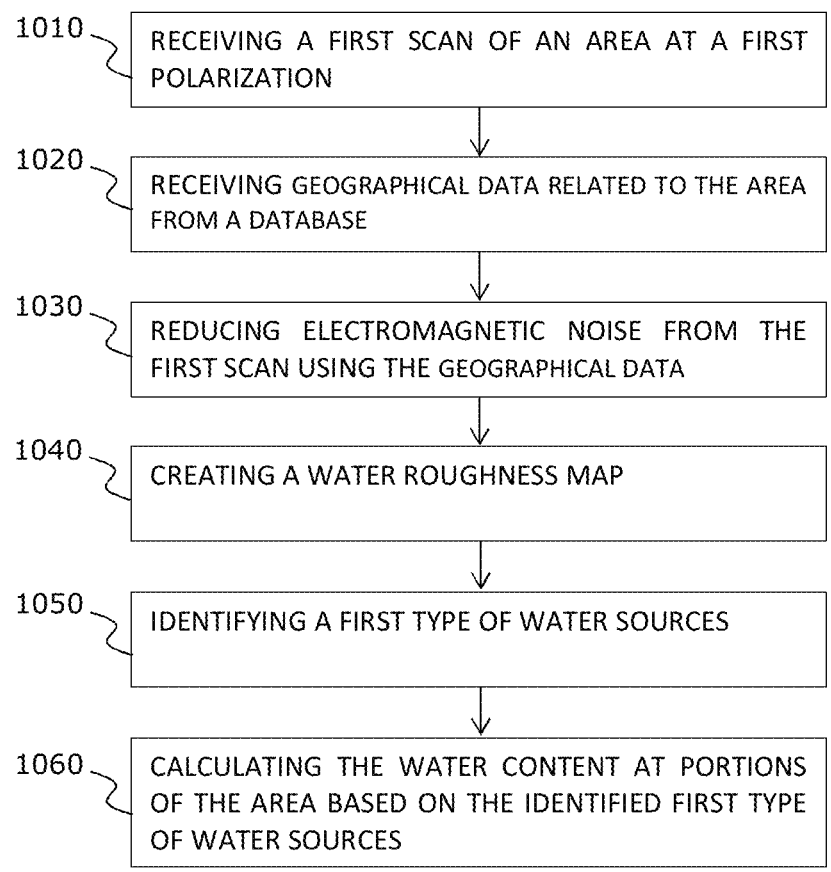
FIG. 10 is a flowchart of an exemplary method of detecting underground water according to some embodiments of the invention.

Reference is made to FIG. 10, a flowchart of a method of remote detecting underground water according to some embodiments of the invention. Embodiments of the method of FIG. 10 may be performed for example by system 100 or by another system. In operation 1010, embodiments may include receiving a first scan of an area at a first polarization. Operation 1010 may be substantially the same as operation 210 of the embodiments of FIG. 2 and may include the operations, steps and equations disclosed above with respect to operation 210.

Figure 11:
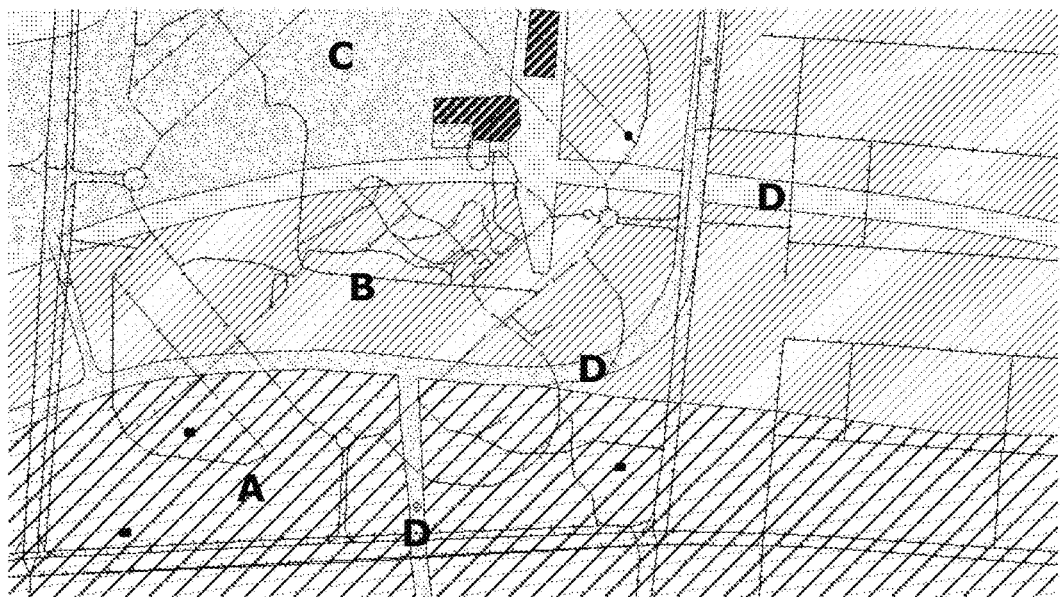
FIG. 11 is an exemplary graphical representation of geographical data according to some embodiments of the invention.

In operation 1020, geographical data related to the area may be received from a database. In some embodiments, the geographical data may include a land cover data related to the area. Exemplary land cover may include types such as: a dense urban area, an urban area, a park, an agricultural area, an industrial area, a village and/or paved area. In some embodiments, the land cover data may include classification of various portions in the scanned area into various land cover types, for example, the land cover types listed above. A graphical representation of a scanned area classified to various land cover types is illustrated in FIG. 11. FIG. 11 is a map of a portion of an area presenting 4 land cover types at different location on the map according to one embodiment. The land coves: at location A may be classified as an industrial area, at location B may be classified as urban area, at location C may be classified as a park and at locations D may be classified as paved areas. Other classifications may be used.

In some embodiments, the geographical data may include a location, length, width and height of objects (e.g., buildings) in the scanned area. For at least some of the buildings in the area the location and dimensions of each building may be included in the geographical data.

In operation 1030, electromagnetic noise may be filtered from the first scan using the geographical data. In some embodiments, filtering the electromagnetic noise may include assigning filtering parameters to each portion of the area based on the land cover type of the classification of the portions of the area. The filtering parameters may be related to the amount of scattering of the microwaves that is typical for each land cover type.

Figure 12:
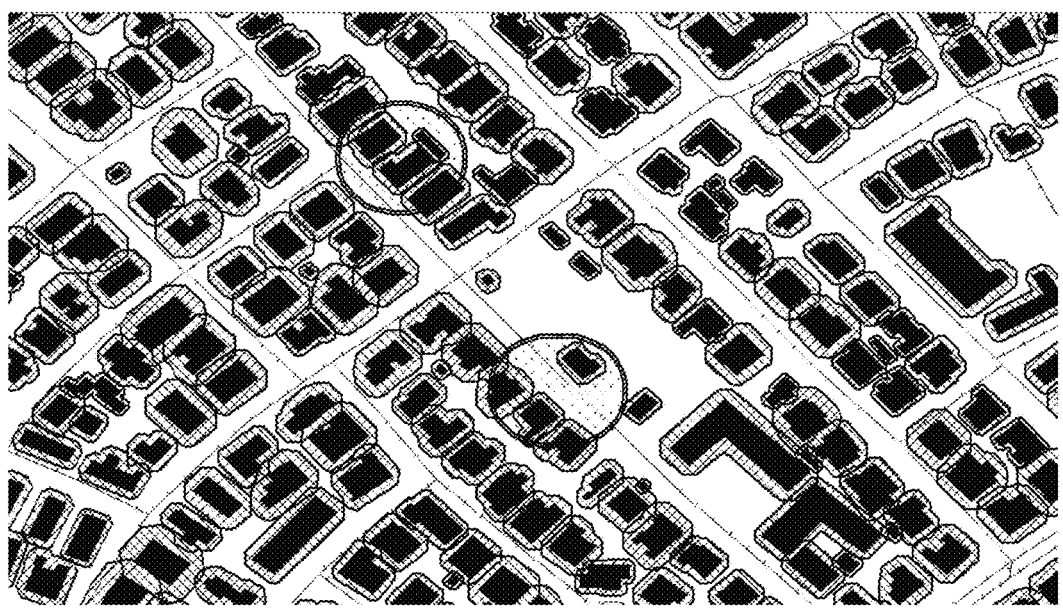
FIG. 12 is an exemplary graphical representation of geographical data according to some embodiments of the invention.

In some embodiments, filtering the electromagnetic noise may include calculating the size and location of blind spots areas in proximity to objects in the area, wherein the objects block microwave reflection from the blind spots areas from reaching the sensor. An exemplary calculation of blind spot areas near a building may be done using for example equation (9).

$$S = \tan \alpha \times Hbl \qquad (9)$$

Wherein S is the size (in m²) of the blind spot area, a is the off-nadir angle from the satellite to the ground and Hbl is the height of the building. A calculation done for 3 stores building resulted in a blind spot area of 4 m2. FIG. 12 is an illustration of calculated blind spot areas created by nearby buildings according to one embodiment. The squared patterned areas around the dark objects are the blind spot areas. These blind spot areas may be used to filter false readings, for example, if an indication is made that there is a leakage of water under an area located in the blind spot area (illustrated as a circle), embodiments may include concluding that these indications are false readings and should be neglected.

Some embodiments may include receiving a second scan of the area at a second polarization, the second scan including second microwave reflections from the area, at a wavelength range of 3.8 cm to 1.3 m, for example, L band and/or P band reflections, the second scan being from the first sensor as discussed with respect to operation 220 of FIG. 2. In some embodiments, filtering the EM noise from the first scan may further include using the second scan, as discussed with respect to operation 230 of FIG. 2.

Operations 1040-1060 may be substantially the same as operations 240-260 of FIG. 2 and may include the steps, operations and equations of operations 240-260. The embodiment of FIG. 10 may include any operation or step that may be included and disclosed with respect to the embodiments of FIG. 2 and/or FIG. 9.

In some embodiments, detecting underground water content may assist in detecting gas leaks from gas pipes. Gas, as a medium, may go undetected by microwave radiation due to its very low dielectric constant, accordingly, a new and innovative way is needed to detect gas leakages using microwave radiation.

Gas (e.g., natural gas or any other type of fluid) is typically transported in gas pipes as an overcritical fluid, around 0° C. at a pressure of around 20-40 bars. Therefore, the transported gas contains almost no water molecules. In some embodiments, when a burst (leakage) of gas happens from the pipe, the pressure may instantly drop from 20-40 bars to an atmospheric pressure, and thus cause a condensation of water at the leakage point. For example, at 20-40 bars the amount of water in the gas may not exceed 400 ppm, while in atmospheric pressure the amount of water may be 10 times higher and reach 4,000 ppm. Accordingly, a continuous leakage of 1,000 Kg/day of gas may result in a condensation of 144 liters/day of water. The condensed water may accumulate in the soil/ground surrounding the pipes thus may be detected using any one of the methods disclosed herein.

Additional amounts of water accumulated due to a gas discharge may be formed during a combustion of the discharged gas, for example, as a result of the following reaction:

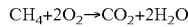

Figure 13:
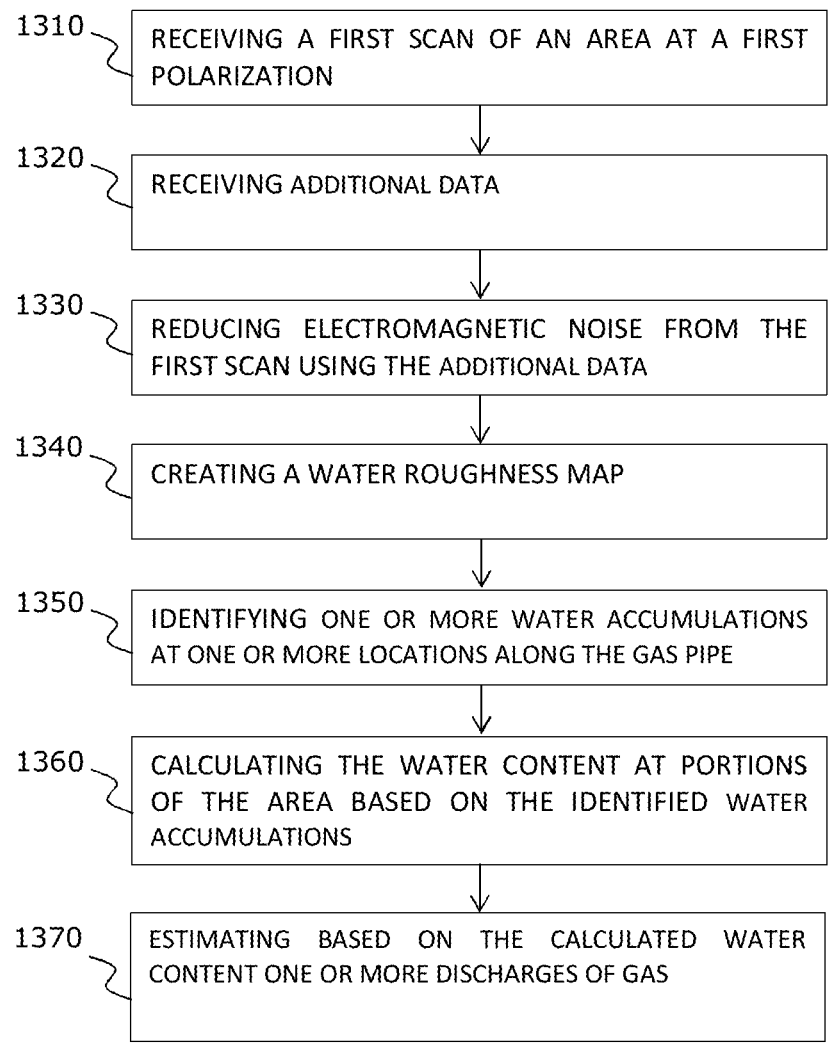
FIG. 13 is a flowchart of a method of detecting underground gas leakage according to some embodiments of the invention.

For example, combustion of 1,000 Kg/day of gas may result in creation of 2,100 liters/day of water In some embodiments, the detected amount of accumulated water may allow estimating the discharge rate of gas leaked from the gas pipe. Reference is now made to FIG. 13 which is a flowchart of a method of detecting underground gas leakage according to some embodiments of the invention. Embodiments of the method of FIG. 13 may be performed for example by system 100 or another suitable system. In operation 1310, a first scan of an area may be received from a first sensor for detecting microwave radiation reflections. The detection may be at a wavelength range of for example 3.8 cm to 1.3 m and the first sensor may be located for example at least 50 meters above the area. In some embodiments, the area may include an underground gas pipe. The first scan may be at a first polarization and may include first microwave reflections of the area at a wavelength range of 3.8 cm to 1.3 m. Operation 1310 may be substantially the same as operation 210 of the embodiments of FIG. 2 and may include the operations, steps and equations disclosed above with respect to operation 210.

In operation 1320, additional data may be received and in operation 1330 electromagnetic noise may be filtered from the first scan using the additional data. In some embodiments, the additional data may include spectral data of at least a portion of the scanned area including the gas pipe. For example, the spectral image may be taken at a wavelength that is absorbed by methane. Such an image by itself may not be able to be used to detect a gas leakage from the first microwave scan. In some embodiments, the optical data may be captured at a wavelength in a range of, for example, between 0.38 μm and 1 cm, as disclosed and discussed with respect to operation 920, of the embodiments of FIG. 9 and filtering the electromagnetic noise may be conducted using the same method disclosed in operation 930 of FIG. 9.

In some embodiments, the additional data may include a second scan of the area at a second polarization, where the second scan may include a second set of microwave reflections from the area in a wavelength range of 3.8 cm to 1.3 m. In some embodiments, the second scan may be from the first sensor and filtering the electromagnetic noise from the first scan may include using the second scan, for example as disclosed and discussed in detail with respect to operations 220 and 230 of the embodiments of FIG. 2.

In some embodiments, a third scan of the area at a second polarization may be received from the first sensor, the third scan including a third set of microwave reflections, at a wavelength range of for example 3.8 cm to 1.3, from the area at a higher resolution than the resolution of the first and second scans, the third scan being from a second sensor for detecting microwave radiation reflections, at a wavelength range of 3.8 cm to 1.3, located coextensive with, at, or attached to the object located at least 50 meters above the area. In some embodiments, electromagnetic noise may be filtered from the third scan using the first and second scans, for example as disclosed above with respect to the embodiments of FIG. 2.

In some embodiments, a fourth scan of the area at a third polarization and a fifth scan in a fourth polarization may be received from the first sensor, where the fourth scan may include a set of fourth microwave reflections from the area, at a wavelength range of for example 3.8 cm to 1.3 the fifth scan may include a set of fifth microwave reflections from the area at a wavelength range of for example 3.8 cm to 1.3. In some embodiments, filtering electromagnetic noise from the first scan may further include using the fourth and fifth scans to filter, for example as disclosed above with respect to the embodiments of FIG. 2.

In some embodiments, the additional data may include geographical data related to the area and/or the gas pipe and filtering the electromagnetic noise may include using the geographical data, for example as disclosed and discussed with respect to operation 1020 and 1030 of the embodiments of FIG. 10.

In operation 1340, a water roughness map may be created based on typical roughness values of a set of types of water sources and the filtered first scan. The water sources may include water accumulations in the vicinity of gas pipes. Operation 1340 may be substantially the same as operation 240 of the method of FIG. 2.

In operation 1350, one or more water accumulations (e.g., collection or accumulation of water) at one or more locations along the gas pipe may be identified using the water roughness map and the filtered first scan. In some embodiments, identifying one or more water accumulations at one or more locations along the gas pipe may be done using methods disclosed with respect to operation 250 of FIG. 2 for identifying a first type of water sources.

In operation 1360 the water content (e.g., the amount of water or the capacity of water) at the one or more locations along the gas pipe may be calculated based on the identified one or more water accumulations. In some embodiments, calculating the water content at the one or more locations along the gas pipe may be conducted using substantially the same methods disclosed in operation 260 of the method of FIG. 2.

In operation 1370, one or more discharge rates of gas leaked from the gas pipe at the one or more locations along the gas pipe may be estimated based on the calculated water content. In some embodiments, estimating the discharge rates of gas leaking from each detected leak, may be based on pre-calculated correlation between water content of and gas discharge rate. The pre-calculated correlation maybe calculated for example using the equation (10); other formulas may be used.

$$D_{WC} \times \alpha = C_{GDR} \tag{10}$$

wherein, $D_{WC}$ is the detected water content, a is a correlation factor (e.g., 1/0.16 or 1/2.32) and $C_{GDR}$ is the calculated gas discharge rate. In some embodiments, α may include a correlation factor for correlating gas discharge with water condensation and/or gas discharge with water as a product of a combustion process.

An example for pre-calculated correlations between detected water content (as water capacity) and gas discharge rate, due to condensation of water is given in table 1 below.

An example for pre-calculated correlation between detected water content (as water capacity) and gas discharge rate, as a product of combustion process of the gas, is given n table 2 below.

TABLE 1

| water content [l/min] | gas discharge rate [Kg/min] |
| --- | --- |
| 0.00 | 0.02 |
| 0.01 | 0.03 |
| 0.01 | 0.05 |
| 0.01 | 0.06 |
| 0.01 | 0.08 |
| 0.02 | 0.10 |
| 0.02 | 0.11 |
| 0.02 | 0.13 |
| 0.02 | 0.15 |
| 0.03 | 0.16 |
| 0.05 | 0.32 |
| 0.08 | 0.48 |
| 0.10 | 0.65 |
| 0.13 | 0.81 |
| 0.15 | 0.97 |
| 0.18 | 1.13 |
| 0.21 | 1.29 |
| 0.23 | 1.45 |
| 0.26 | 1.61 |
| 0.39 | 2.42 |
| 0.52 | 3.23 |
| 0.77 | 4.84 |
| 1.03 | 6.45 |
| 1.29 | 8.07 |
| 1.55 | 9.68 |
| 1.81 | 11.29 |
| 2.07 | 12.91 |
| 2.32 | 14.52 |
| 2.58 | 16.13 |
| 5.16 | 32.27 |
| 7.74 | 48.40 |
| 10.33 | 64.54 |
| 12.91 | 80.67 |
| 129.07 | 806.70 |

TABLE 2

| water content [l/min] | gas discharge rate [Kg/min] |
| --- | --- |
| 0.23 | 0.1 |
| 0.46 | 0.2 |
| 0.70 | 0.3 |
| 0.93 | 0.4 |
| 1.16 | 0.5 |
| 2.32 | 1.0 |
| 4.64 | 2.0 |
| 6.96 | 3.0 |
| 9.28 | 4.0 |
| 11.60 | 5.0 |
| 13.92 | 6.0 |
| 16.24 | 7.0 |
| 18.56 | 8.0 |
| 20.88 | 9.0 |
| 23.20 | 10.0 |
| 46.40 | 20.0 |
| 69.60 | 30.0 |
| 92.80 | 40.0 |
| 116.00 | 50.0 |
| 232.00 | 100.0 |
| 464.00 | 200.0 |
| 696.00 | 300.0 |
| 928.00 | 400.0 |
| 1,160.00 | 500.0 |
| 2,320.00 | 1,000.0 |
| 4,640.00 | 2,000.0 |
| 6,960.00 | 3,000.0 |
| 9,280.00 | 4,000.0 |
| 11,600.00 | 5,000.0 |
| 23,200.00 | 10,000.0 |
| 46,400.00 | 20,000.0 |
| 69,600.00 | 30,000.0 |
| 92,800.00 | 40,000.0 |
| 116,000.00 | 50,000.0 |

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method of detecting underground gas leakage, comprising:
   receiving a first scan of an area comprising an underground gas pipe at a first polarization, the first scan including first microwave reflections of the area at a wavelength range of 3.8 cm to 1.3 m;
   the first scan being from a first sensor for detecting microwave radiation reflections at a wavelength range of 3.8 cm to 1.3 m, the sensor being located at least 50 meters above the area;
   receiving additional data;
   filtering electromagnetic noise from the first scan using the additional data;
   creating a water roughness map based on typical roughness values of a set of types of water sources and the filtered first scan;
   identifying one or more water accumulations at one or more locations along the gas pipe using the water roughness map and the filtered first scan; and
   calculating the water content at the one or more locations along the gas pipe based on the identified one or more water accumulations,
   wherein the additional data comprises a second scan of the area at a second polarization, the second scan including second microwave reflections from the area at a wavelength range of 3.8 cm to 1.3 m, the second scan being from the first sensor,
   and wherein filtering the electromagnetic noise from the first scan further comprises using the second scan,
   and wherein filtering electromagnetic noise comprises at least one of:
   filtering electromagnetic reflection noise received from solid objects located in the scanned area, and
   filtering electromagnetic bouncing reflection noise from solid objects located in the scanned area.

2. The method of claim 1 further comprising estimating based on the calculated water content one or more discharge rates of gas leaked from the gas pipe at the one or more locations along the gas pipe.

3. The method of claim 2, wherein estimating the discharge rates of gas leaking from each detected leak, is based on a pre-calculated correlation between water content of and an amount of gas.

4. The method of claim 1, wherein the additional data is spectral data of at least a portion of the scanned area comprising the gas pipe, the spectral data being captured at a wavelength in a range between 0.38 μm to 1 cm.

5. The method of claim 4, wherein the spectral data is received from at least one of:
   satellite-borne spectral imagery and airborne spectral imagery.

6. The method of claim 1, further comprising:
converting the first and second microwave reflections, at a wavelength range of 3.8 cm to 1.3 m, from gray scale levels to intensity levels.

7. The method of claim 1 wherein the first and second scans have the same resolution.

8. The method of claim 7, comprising receiving a third scan of the area at a second polarization, the third scan including a third set of microwave reflections, at a wavelength range of 3.8 cm to 1.3, from the area at a higher resolution than the resolution of the first and second scans, the third scan being from a second sensor for detecting the microwave radiation reflections, at a wavelength range of 3.8 cm to 1.3, located at least 50 meters above the area.

9. The method of claim 8, comprising filtering electromagnetic noise from the third scan using the first and second scans.

10. The method of claim 8, wherein the first polarization is a horizontal polarization and the second polarization is a vertical polarization.

11. The method of claim 8, comprising:
receiving a fourth scan of the area at a third polarization, the fourth scan including fourth microwave reflections from the area, at a wavelength range of 3.8 cm to 1.3 m; and
receiving a fifth scan of the area at a fourth polarization, the fifth scan including fifth microwave reflections from the area at a wavelength range of 3.8 cm to 1.3 m, the fourth and fifth scans being from the first sensor,
wherein, filtering electromagnetic noise from the first scan comprises using the fourth and fifth scans to filter.

12. A system for detecting underground gas leakage, comprising:
a processor; and
a non-transitory computer readable medium having stored thereon computer-executable instructions which when executed by the processor cause the processor to:
receive a first scan of an area comprising an underground gas pipe at a first polarization, the first scan including first microwave reflections of the area at a wavelength range of 3.8 cm to 1.3 m;
the first scan being from a first sensor for detecting microwave radiation reflections at a wavelength range of 3.8 cm to 1.3 m, the sensor being located at least 50 meters above the area;
receive additional data;
filter electromagnetic noise from the first scan using the additional data;
create a water roughness map based on typical roughness values of a set of types of water sources and the filtered first scan;
identify one or more water accumulations at one or more locations along the gas pipe using the water roughness map and the filtered first scan; and
calculate the water content at the one or more locations along the gas pipe based on the identified one or more water accumulations,
wherein the additional data comprises a second scan of the area at a second polarization, the second scan including second microwave reflections from the area at a wavelength range of 3.8 cm to 1.3 m, the second scan being from the first sensor,
and wherein filtering the electromagnetic noise from the first scan further comprises using the second scan,
and wherein filtering electromagnetic noise comprises at least one of:
filtering electromagnetic reflection noise received from solid objects located in the scanned area; and
filtering electromagnetic bouncing reflection noise from solid objects located in the scanned area.

13. The system of claim 12, wherein the instructions further cause the processor to estimate based on the calculated water content one or more discharge rates of gas leaked from the gas pipe at the one or more locations along the gas pipe.

14. The method of claim 13, estimating the discharge rates of gas leaking from each detected leak, is based on pre-calculated correlation between water content of and an amount of gas.

15. The system of claim 12, wherein the additional data is spectral data of at least a portion of the scanned area comprising the gas pipe, the spectral data being captured at a wavelength in a range between 0.38 µm to 1 cm received from at least one of: a satellite-borne spectral imagery and an airborne spectral imagery.

* * * * *